United States Patent [19]

Zaloga et al.

[11] Patent Number: 5,576,287
[45] Date of Patent: Nov. 19, 1996

[54] METHOD FOR TREATING ACUTE RENAL DISEASE AND FAILURE

[75] Inventors: Gary P. Zaloga; Pamela Roberts, both of Winston-Salem, N.C.

[73] Assignee: Wake Forest University, Winston-Salem, N.C.

[21] Appl. No.: 236,501

[22] Filed: Apr. 29, 1994

[51] Int. Cl.$^6$ .......... A61K 38/00; A61K 31/415; A61K 31/40; A61K 31/195

[52] U.S. Cl. .......... 514/2; 514/400; 514/423; 514/561; 514/564; 514/566

[58] Field of Search .......... 514/2, 561, 566, 514/423, 564, 400

[56] References Cited

U.S. PATENT DOCUMENTS

| | | | |
|---|---|---|---|
| 4,357,343 | 11/1982 | Madsen et al. | 514/561 |
| 4,491,589 | 1/1985 | Dell et al. | 514/561 |
| 4,752,619 | 6/1988 | Walser et al. | 514/564 |
| 4,792,549 | 12/1988 | Takahashi et al. | 514/400 |
| 4,957,938 | 9/1990 | Anderson et al. | 514/412 |
| 5,108,767 | 4/1992 | Mulchandani et al. | 426/72 |
| 5,122,515 | 6/1992 | Smith et al. | 514/19 |
| 5,132,113 | 7/1992 | Lucá | 424/195.1 |
| 5,175,144 | 12/1992 | Walser | 514/2 |
| 5,356,873 | 10/1994 | Mark et al. | 514/2 |

FOREIGN PATENT DOCUMENTS 974388  11/1964  United Kingdom.

OTHER PUBLICATIONS

*The Clintec Nutrition Enteral Product Reference Guide,* Clintec Nutrition Company, pp. 1–3 (1990).
Alvestrand et al, *Renal Diseases,* 29, pp. 531–557 (1990).
Oldrizzi et al, *Nutrition and the Kidney: How to Manage Patients with Renal Failure,* NCP, vol. 9, No. 1, pp. 3–10 (1994).

*Primary Examiner*—Raymond Henley, III
*Attorney, Agent, or Firm*—Dann, Dorfman, Herrell and Skillman

[57] ABSTRACT

A nutritional composition and methods of using same for treating and preventing renal failure is provided. The nutritional composition includes a therapeutically effective amount of a source protein including meat proteins. Furthermore, the nutritional composition includes a therapeutically effective amount of specific amino acids, peptides, and/or polypeptides. The specific amino acids, peptides and polypeptides are selected such that they counteract a pathophysiologic mechanism contributing to the renal failure.

17 Claims, No Drawings

METHOD FOR TREATING ACUTE RENAL DISEASE AND FAILURE

BACKGROUND OF THE INVENTION

The present invention relates to nutritional formulations for the support and therapy of individuals. More specifically, the present invention relates to nutritional compositions and methods of using same for preventing or treating renal disease and failure.

Acute renal failure ("ARF") refers to the clinical conditions associated with rapid, steadily increasing azotemia, with or without oliguria (<500 mL/day). The cause of ARF can be grouped into three diagnostic categories: prerenal (inadequate renal perfusion); postrenal (obstruction); and renal. *Merck Manual*, 16th Edition, p. 1661 (1992).

The pathophysiology of ARF is complex and multifactorial. Current concepts suggest that ARF may result from the following mechanisms: (1) direct renal tubular injury; (2) renal ischemia; and (3) intra-tubular obstruction.

Direct as well as indirect toxic effects upon the kidney causes direct renal tubular injury. Examples of toxic antibiotics that can cause adverse reactions are aminoglycosides. Tubular injury may also arise following rhabdomyolysis. Free radicals, cytokines, and other toxins produced in response to a drug or injury mediate the indirect toxic effect upon the kidney.

Renal ischemia is one of the most common intrinsic renal causes of ARF. In general, renal ischemia refers to localized tissue hypoxia within kidneys that results from the obstruction of the inflow of blood or low blood oxygen levels. A number of conditions cause renal ischemia including diminished renal blood flow (e.g. shock states, amphotericin B), low cardiac output, and when the oxygen demand is greater than supply. In addition, renal artery vasoconstriction, increased renal vascular resistance, and abnormal tubuloglomerular feedback (TGF) may cause renal ischemia.

In addition to the previous two mechanisms, intra-tubular obstruction may also cause ARF. Intra-tubular obstruction may result from obstructions caused by such substances as cellular debris or protein.

Clinically, ARF results in diminished glomerular filtration and reduced secretion of metabolic waste products, water, and electrolytes. Fluid overload, electrolyte imbalances and the uremic syndrome result in organ dysfunction. Organ dysfunction may ultimately result in death.

Dialysis is commonly used to treat many of the metabolic disturbances of ARF. Dialysis is generally started as soon as possible after the diagnosis is established, since patients with advanced azotemia may deteriorate in an unpredictable manner. Unfortunately, however, morbidity from dialysis and persistence of renal failure are common.

Therefore, a need exists for a new mode of therapy for the prevention and treatment of ARF.

SUMMARY OF THE INVENTION

The present invention provides a nutritional composition as well as methods of using same for treating patients suffering from or at risk of acute renal failure. To this end, the present invention uniquely utilizes nutrients with specific physiologic actions upon the kidney. The various nutrients are combined to prevent and minimize renal injury from a variety of insults and to reduce occurrence or help speed recovery from ARF.

The present invention provides an improved nutritional composition for treating acute renal failure. The nutritional composition includes a therapeutically effective amount of a source protein that is based, at least in part, on meat proteins. The source protein may consist of intact protein or hydrolyzed protein (i.e. peptides produced by protein degradation). In addition, the nutritional composition includes a therapeutically effective amount of specific amino acids, peptides, and/or polypeptides. The specific polypeptides, peptides and amino acids are selected to counteract a pathophysiologic mechanism contributing to the renal failure.

In an embodiment, the source protein further includes milk and vegetable proteins.

In an embodiment, the nutritional composition further includes a base composition containing vitamins, minerals, and trace elements.

In an embodiment, the nutritional composition includes specific nutrients (e.g. amino acids, peptides, and/or polypeptides) that effectively counteract pathophysiologic mechanisms causing the acute renal failure. Examples of such pathophysiological mechanisms include direct renal tubular injury, renal ischemia, and intra-tubular obstruction.

The present invention also provides a method for treating and preventing renal failure. The method includes the step of administering to a patient having renal failure or at risk of same a nutritional composition comprising a therapeutically effective amount of a source protein including meat proteins.

In an embodiment, the protein includes milk and vegetable proteins.

Likewise, the present invention further provides a method for treating and preventing renal failure comprising the step of administering to a renal patient a therapeutically effective amount of specific amino acids, peptides or polypeptides. Depending on the type of pathophysiological mechanism being targeted, suitable amino acids, peptides or polypeptides are selected to counteract such pathophysiologic mechanisms.

Still further, the present invention provides a method for treating and preventing renal failure comprising the step of administering to a renal patient a composition that includes at least 15% of its caloric content as protein.

An advantage of the present invention is that it provides an improved nutritional composition for the treatment of acute renal failure.

Another advantage of the present invention is that the nutritional composition utilizes protein precursors and/or degradation products, such as amino acids and peptides, for their physiologic actions (i.e. bioactivity) and not merely as substrates for protein synthesis.

Still further, an advantage of the present invention is that the nutritional composition effectively counteracts various pathophysiologic mechanisms that contribute to acute renal failure.

Moreover, an advantage of the present invention is that it provides a therapy for the specific treatment of acute renal failure that focuses upon improving renal function.

Yet another advantage of the present invention is that it recognizes the unique advantage of utilizing meat proteins for treating renal failure.

Another advantage of the present invention is that it not only provides a method for treating renal failure but also a method for preventing same.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides an active nutritional composition for preventing and treating acute renal failure. The invention utilizes a source protein including meat proteins that effectively increase renal blood flow and glomerular filtration rate. In addition, the present invention utilizes specific amino acids, peptides, or polypeptides that counteract various types of pathophysiologic mechanisms contributing to acute renal failure.

Unlike prior treatments, the present invention provides a therapy for preventing renal failure or improving renal function, as opposed to simply providing supportive therapy. The nutritional composition of the present invention includes nutrients that effectively counteract the mechanisms causing acute renal failure.

Nutrients may prevent or diminish ARF by interfering with the pathophysiological mechanisms responsible for renal damage. For instance, nutrient administration may alter direct tubular injury, diminish renal ischemia, and prevent intra-tubular obstruction. Still further, the nutritional composition can improve renal blood flow, glomerular filtration rate, and excretory function. The nutritional composition of the present invention may also decrease the need for dialysis, improve return of renal function, shorten hospital stay, and improve functional outcome.

The nutritional composition of the present invention utilizes a source protein component including meat proteins. As one skilled in the art will appreciate, the source protein can be administered in a variety of forms without departing from the scope of the present invention. The source protein can be an intact protein and/or hydrolyzed protein (i.e. peptides produced by protein degradation.)

Proteins (via their constituent peptides and amino acids) are direct vasodilators of the renal arteries and may inhibit tubulo-glomerular feedback. As a result thereof, such proteins can effectively increase renal plasma flow and glomerular filtration rate.

The quantity of the source protein effects improved renal function. Currently, patients with renal injuries are usually administered low quantities of protein. For example, approximately 0.7–1.0 grams per kilogram body weight of protein is administered per day to minimize production of urea and azotemia. See, for example, L. Oldrizzi et al., *Nutrition in Clinical Practice*, 9 (1): 3–10 (1994); and A. Albestrand and J. Bergstrom, Chapter 29, pp. 531–557 in Nutrition and Metabolism in Patient Care (J. Kinney et al., eds.), W. B. Saunders, Philadelphia (1988). However, the inventors have discovered that administering high levels of the source protein improves renal blood flow and renal function (especially glomerular filtration rate).

Protein administration may also enhance the rate of recovery from acute renal failure. Protein administration stimulates renal protein synthesis and phospholipid synthesis in regenerating renal tubular cells. High protein diets induce hypertrophy of kidneys. In an embodiment, the nutritional composition includes at least 20% of its caloric content as the source protein. In a further embodiment, approximately 15% to 35%, based on caloric content, of the composition is the source protein.

In addition to the quantity of protein, the specific source of protein also affects renal function. Current feeding formulas commonly incorporate milk (i.e. casein and whey) and vegetable (i.e. soy) based protein sources. In contrast thereto, the inventors have found that meat derived proteins increase renal blood flow and glomerular filtration rate to a greater extent than the previously utilized milk and vegetable based protein sources. The effects of these protein sources may be mediated via peptides and amino acids generated from digestion of the source protein.

While the use of meat proteins alone may improve renal function, supplementing the meat protein diet with amino acids, peptides or polypeptides having specific physiologic actions provides added benefits. The nutritional composition of the present invention utilizes nutrients with specific physiologic actions upon the kidney. These nutrients, in combination, prevent and minimize renal injury from a variety of insults and help speed recovery from ARF.

As set forth above, ARF may result from the following pathophysiological mechanisms: (1) direct tubular injury; (2) renal ischemia; and (3) intra-tubular obstruction. The nutritional composition of the present invention utilizes specific amino acids, peptides, or polypeptides that counteract these mechanisms to thereby prevent ARF. In addition to interfering with the natural progression of these mechanisms, use of these amino acids, peptides, or polypeptides may also improve return of renal function.

Nutrients that interfere with binding of toxins to renal tubular cells or reduce free radical/oxidant damage may prevent renal tubular damage. For example, poly-lysine, poly-arginine, and poly-aspartate can antagonize aminoglycoside binding to renal tubular cells and may be useful for preventing aminoglycoside-induced renal toxicity.

Certain nutrients may act as scavengers of oxygen free radicals and reduce cellular injury. Carnosine (beta-alanine-histidine) can scavenge free radicals and may prevent free radical induced renal injury. Taurine is an amino acid with anti-oxidant properties. Cysteine is a precursor for anti-oxidant compounds such as glutathione (composed of glycine, cysteine, and glutamate). Glycine and alanine also possess cytoprotective properties. These substances may be utilized to prevent injury to the kidney.

In addition to tubular injury, renal damage may result from renal ischemia due to diminished blood flow to the kidney (i.e. vasoconstriction, excess tubulo-glomerular feedback). Specific amino acids, peptides, or polypeptides may be selected to antagonize vasoconstriction of the renal artery and/or diminished glomerular filtration.

Some amino acids (i.e., glycine, glutamine, proline, beta-alanine, alanine, taurine, arginine) and peptides (i.e. carnosine, cyclo-histidine-proline) have specific renal vasodilator actions. Arginine is the precursor of nitric oxide and is responsible for endothelium-dependent vasodilation. Endothelium-dependent vasodilation is attenuated following ischemia or hypoxia. Therefore, supplementing the nutritional composition with these amino acids and peptides can improve renal blood flow and glomerular filtration rates in patients with acute renal failure.

Nutrients that reduce cellular oxygen consumption may also limit ischemic damage by improving the oxygen delivery/consumption ratio. Thus, compounds such as carnosine and histidine that limit hormonal action (i.e. antidiuretic hormone) and diminish cellular activity (i.e. cyclic adenosine monophosphate generation) may improve recovery from acute renal failure. Amino acids and small peptides may also serve as cellular fuels and help recovery from injury. Glutamine is an important energy source for lymphocytes and fibroblasts. Alanine is an important substrate for glucose synthesis.

Amino acids and peptides may also diminish cellular injury by modulating intracellular calcium levels. Elevated intracellular calcium has been linked to organ injury following ischemia and infection. Taurine can modulate calcium entry into cells.

Still further, the present invention may be utilized to counteract intra-tubular obstruction. Amino acids that impair tubular reabsorption of various substances may minimize intra-tubular obstruction. Maintenance of high intra-tubular pressures and flow may also prevent tubular obstruction. Lysine and arginine impair renal tubular protein absorption. Whereas, histidine and beta-alanine impair salt and water absorption. Carnosine also increases renal salt and water excretion. These amino acids and peptides containing the amino acids cause a natriuresis and diuresis. Impermeant solutes (such as amino acids and peptides) may also limit renal cell injury by minimizing osmotic swelling due to damaged cell membranes and altered membrane ion pump activity (which occur during acute renal failure). The net effect of these agents is to minimize tubular obstruction.

Moreover, certain amino acids, peptides, or polypeptides may also improve the rate of recovery from acute renal function. For example, arginine and carnosine improve healing of injured tissue. Arginine, proline, and lysine are substrates for collagen synthesis. Arginine is a precursor of nitric oxide (important stimulant of wound healing) and may also stimulate secretion of growth hormone. All of these nitrogen compounds have the potential for stimulating repair and improving recovery from acute renal failure.

Pursuant to the present invention, a variety of different amino acids, peptides, or polypeptides may be chosen to counteract certain pathophysiological mechanisms. By way of example, and not limitation, the renal effect of suitable amino acids, peptides, or polypeptides (discussed supra) is categorized below:

Cytoprotective: carnosine, glutathione, taurine, cysteine, glycine, and alanine;

Inhibitors of tubular reabsorption: poly-lysine (2–10 amino acids), poly-arginine (2–10 amino acids), and poly-aspartate (2–10 amino acids);

Vasodilators: glycine, glutamine, proline, beta-alanine, alanine, taurine, arginine, carnosine, and cyclo-histidine-proline;

Decrease oxygen consumption: histidine and carnosine;

Cellular fuels: glutamine and alanine;

Calcium entry blocker: taurine;

Decrease tubular obstruction: lysine, arginine, histidine, beta-alanine, and carnosine; and Improve renal recovery: proline, lysine, and carnosine.

By way of example, and not limitation, suitable nutritional compositions that may be utilized pursuant to the present invention will now be given.

Nutritional Composition #1

A suitable composition that may be utilized to prevent renal ischemic states (such as ischemia, hypotension, and shock), amphotericin B, nonsteroidal antiinflammatory drugs, radiocontrast dye, and rhabdomyolysis, is as follows. Notably, a similar formula may also be utilized to improve recovery from acute renal failure. The composition includes:

Source protein (50–100 g/L) composed of meat/vegetable/milk proteins

Amino acids in suprapysiologic levels (5–15 g/L): glycine, arginine, glutamine, alanine, histidine, taurine, beta-alanine, cysteine, proline, and lysine Peptides in suprapysiologic levels (5–15 g/L): poly-arginine, carnosine, cyclo-histidine-proline, and glutathione.

Nutritional Composition #2

A nutritional composition that may be utilized to protect against aminoglycoside toxicity would include the same formulations set forth in composition #1. However, the nutritional composition would also include an inhibitor of aminoglycoside binding. Examples of suitable inhibitors include: poly-lysine; poly-aspartate; and poly-arginine.

In addition to the use of a source protein and suitable amino acids, peptides, or polypeptides, the nutritional composition may also include a base composition, thereby providing a complete nutritional supplement. In an embodiment, the base composition includes the recommended daily intake of vitamins, minerals, and trace elements. Preferably, the base composition is low in magnesium and potassium.

By way of example, and not limitation, an example of a suitable formula that may be used pursuant to the present invention is as follows:

Protein (105 g/l; 33% of calories)

| | |
|---|---|
| Casein or whey | 20 g/l |
| Beef | 20 g/l |
| Carnosine | 7.5 g/l |
| Glycine | 5 g/l |
| Arginine | 7.5 g/l |
| Glutamine | 5 g/l |
| Alanine | 5 g/l |
| Histidine | 5 g/l |
| Taurine | 5 g/l |
| Cysteine | 5 g/l |
| Proline | 5 g/l |
| Lysine | 5 g/l |
| Glutathione | 5 g/l |
| Cyclo-his-pro | 5 g/l |

Carbohydrate: Maltodextrin, Starch 120 g/l (38% of calories)

Fat: MCT Oil, Sunflower Oil or Soy Oil 40 g/l (29% of calories)

The present invention further provides methods for treating and preventing renal failure. The nutritional compositions of the present invention may be administered either orally, enterally, or parenterally.

With respect to the treatment aspect, the nutritional composition may be utilized in treating acute renal failure following shock, rhabdomyolysis, and drug administration. Shock may result from trauma, burns, infection, cardiac insufficiency, or hemorrhage. Among others, drug administration may include aminoglycoside, antibiotics, amphotericin B, radiocontrast dye, nonsteroidal anti-inflammatory drug, and cyclosporine. Still further, the nutritional composition of the present invention may also be utilized to prevent renal failure. The nutritional composition may be administered as a prophylaxis against acute renal failure from the above mentioned causes. Likewise, the nutritional composition may also be administered as a preventive step after renal transplants.

By way of example, and not limitation, experimental results obtained from administering the nutritional composition to experimental animals suffering from renal failure will now be given.

Example #1

The nutritional composition #1 was administered to rats suffering from rhabdomyolysis induced renal failure. The blood urea nitrogen (BUN) levels in the rats were measured to determine the effect of the nutritional composition. As the results illustrate in Table 1, the nutritional composition of the present invention improves survival and prevents renal injury.

TABLE 1

| Formula Group | Survival | BUN (mg/dl) |
|---|---|---|
| Formula (n = 18 animals) | 78% | 47 |
| Control (n = 17 animals) | 35% | 127 |

Example #2

This example illustrates the in-vivo and in-vitro administration of the amino acid histidine. The results demonstrate histidine's ability to alter metabolic activity within the kidney and increase urine output. Specifically, the in-vivo data (see Table 2) illustrates that histidine increases water excretion and reduces renal cyclic adenosine monophosphate ("cAMP") production (decreases metabolic activity).

TABLE 2

| GROUP | Urine output (ml/hr) | Urinary cAMP (pg/ml) |
|---|---|---|
| Histidine (n = 6) | 13.4 | 44 |
| Saline Control (n = 6) | 3.0 | 152 |

Likewise, the in-vitro studies (see Table 3) conducted in isolated renal cells illustrates that histidine decreases cAMP generation and blocks the action of antidiuretic hormone (DDAVP).

TABLE 3

| GROUP | cAMP (pg/ml) | cAMP response to DDAVP |
|---|---|---|
| Histidine (n = 6) | 0.19 | 0.27 |
| Saline (n = 6) | 0.46 | 1.04 |

Example #3

In addition to preventing and treating acute renal failure, the nutritional composition of the present invention can also provide protective effects upon other organs of the body. This example illustrates such protective effects upon the liver of a rat.

In this example, a high protein enteral feeding formula of the present invention was administered to rats suffering liver damage. The enteral formula did not contain supplemental amino acids but did contain hydrolyzed proteins.

To determine the protective ability of the formula, the level of SGOT and SGPT were measured (see Tables 4-5). SGOT and SGPT are liver enzymes that increase in the blood when the liver is damaged.

TABLE 4

| Hemorrhage Study | sGOT (U/L) | sGPT (U/L) |
|---|---|---|
| Formula (n = 10) | 551 | 161 |
| Control (n = 10) | 1605 | 726 |

TABLE 5

| Endotoxin Study | sGOT (U/L) | sGPT (U/L) |
|---|---|---|
| Formula (n = 10) | 788 | 116 |
| Control (n = 10) | 1049 | 300 |

As the results illustrate, the enteral formula protects the liver from injury following hemorrhage and endotoxin injection (a model of sepsis).

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for treating or preventing acute renal failure comprising the step of administering to a patient having acute renal failure or at risk of same a nutritional composition comprising a source protein including meat proteins, in an amount effective to increase renal blood flow and glomerular filtration rate in said patient.

2. The method of claim 1 wherein the source protein further includes milk and vegetable proteins.

3. The method of claim 1 wherein the nutritional composition is administered enterally.

4. The method of claim 1 wherein the nutritional composition is administered parenterally.

5. The method of claim 1 wherein said composition further comprises a therapeutically effective amount of a nutrient chosen to counteract a pathophysiologic mechanism contributing to the renal failure.

6. The method of claim 1 wherein said composition further comprising a base composition including vitamins, minerals, and trace elements.

7. A method for treating or preventing renal failure comprising the step of administering to a renal patient a nutritional composition including an effective amount of a nutrient which counteracts at least one pathophysiologic mechanism contributing to said renal failure, selected from the group consisting of direct renal tubular injury, renal ischemia and intratubular obstruction.

8. The method of claim 7 wherein the nutrient is selected from a group consisting of: amino acids; peptides; and polypeptides.

9. The method of claim 7 wherein said comopsition further comprising a base composition including vitamins, minerals, trace elements.

10. The method of claim 7 wherein the nutritional composition is administered enterally.

11. The method of claim 7 wherein the nutritional composition is administered parenterally.

12. A method for treating or preventing renal failure comprising the step of administering to a patient suffering from renal failure or at risk of same a nutritional composition including at least 15%, based on caloric content, of a source protein.

13. The method of claim 12 wherein the source protein includes meat, milk and vegetable proteins.

14. The method of claim 12 wherein the nutritional composition is administered enterally.

15. The method of claim 12 wherein the nutritional composition is administered parenterally.

16. The method of claim 12 wherein said composition further comprising a base composition including vitamins, minerals, and trace elements.

17. The method of claim 12 wherein said composition further comprising a therapeutically effective amount of a nutrient chosen to counteract a pathophysiologic mechanism contributing to the renal failure.

* * * * *